United States Patent [19]
Shimoji

[11] Patent Number: 5,928,220
[45] Date of Patent: Jul. 27, 1999

[54] CORDLESS DENTAL AND SURGICAL LASER

[76] Inventor: Yutaka Shimoji, 2125 University Ct., Clearwater, Fla. 34624

[21] Appl. No.: 08/872,085

[22] Filed: Jun. 10, 1997

[51] Int. Cl.⁶ .................................................. A61B 17/36
[52] U.S. Cl. ................................. 606/2; 606/13; 606/17; 607/89; 433/29; 433/141; 372/9
[58] Field of Search ......................... 606/2, 9, 10, 13–17; 607/88, 89, 90, 92; 433/141, 216, 29; 250/493.1, 496.1, 505.1; 372/9, 10, 20, 23, 75, 69; 362/109, 119, 120

Primary Examiner—Linda C. M. Dvorak
Assistant Examiner—Bryan K. Yarnell

[57] ABSTRACT

A compact, hand-held, rechargeable, tunable, self-contained laser instrument is presented for use in dentistry, oral surgery, orthopedic surgery, and other medical procedures such as sterilization and curing of photo-polymerizable materials. The inventive instrument includes microchip lasers that consume at most 10 Watts and generate a peak output laser beam power of at least 20 mWatts that is adjustable to the light absorbing characteristics of the target material. Laser microchips, pumping laser, thermo-electric heat exchanger, rechargeable batteries, and laser optics are all contained within the same housing which is cordless, lightweight, and inexpensive to manufacture.

14 Claims, 2 Drawing Sheets

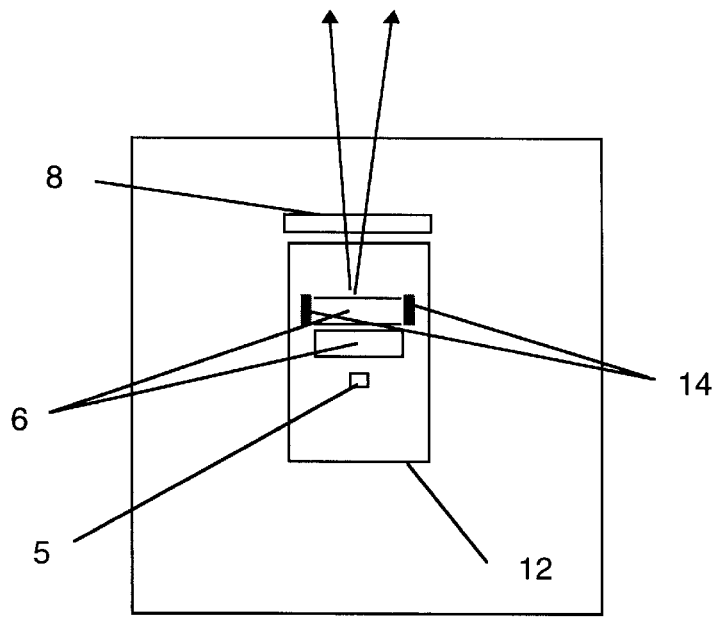
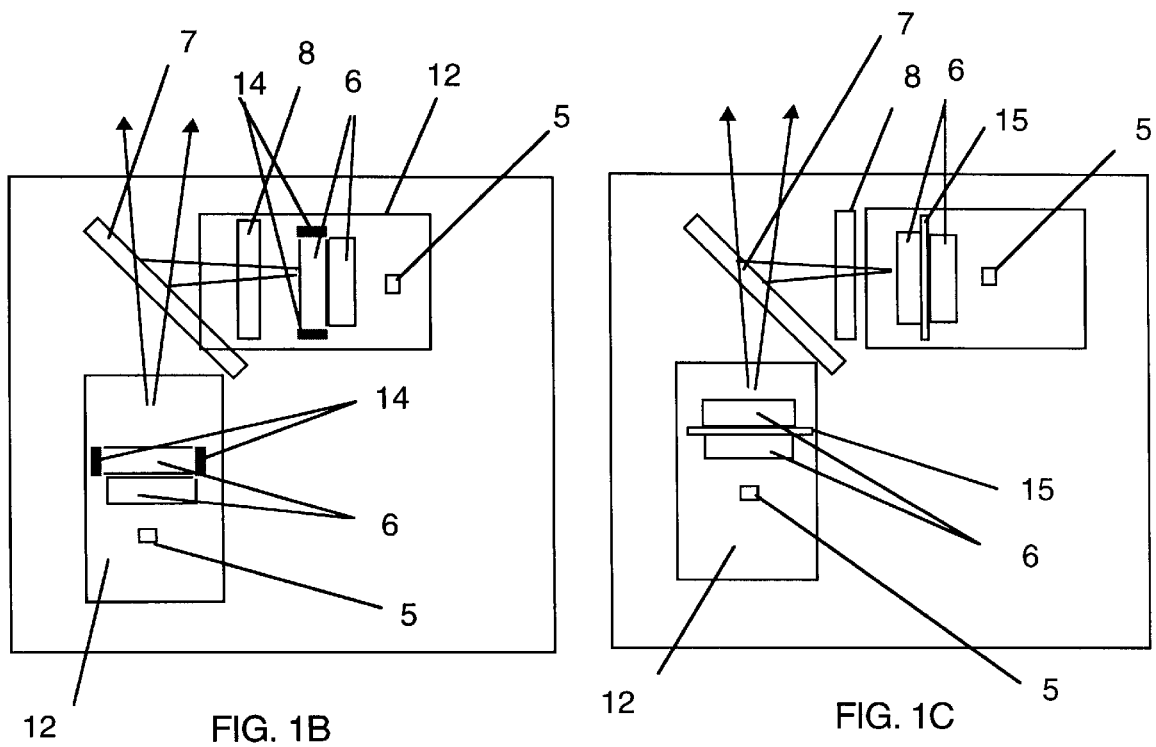
FIG. 1A
FIG. 1B
FIG. 1C 5,928,220

CORDLESS DENTAL AND SURGICAL LASER

BACKGROUND OF THE INVENTION

The present invention relates to microchip dental and surgical laser instruments which are portable, hand-held, cordless, rechargeable and compact. Known dental and surgical lasers are large and connected to hand-held instruments by power, coolant, and optical fiber cables. They are inefficient with a gas filled plasma tube, with wall plug efficiency below 0.01%, and require power consumption exceeding 2000 Watts.

Goldsmith et al. in U.S. Pat. No. 5,334,016 discloses an argon laser for curing dental materials in combination with a helium-neon laser. This system requires a separate housing with forced-air cooling, and a fiber optic cable to deliver the laser beam to a separate hand-held unit. The laser wavelength is not matched to the peak absorption wavelength of the composite to be cured.

Badoz et al. in U.S. Pat. No. 5,388,987, Topel in U.S. Pat. No. 5,548,604, and Cipolla in U.S. Pat. No. 5,616,141 all disclose dental laser units. However, they are all large stationary units connected to separate hand-held units by optic fiber and power cables. These are not cordless units. The wavelength of these lasers are not matched to the peak absorption wavelength of the material to be cured, so much energy is wasted.

Therefore, there remains a need to develop a compact, self-contained, efficient, cordless, rechargeable dental curing laser and surgical laser instrument which can be produced at low cost.

SUMMARY OF THE INVENTION

A self-contained, portable, hand-held, rechargeable, cordless laser instrument for dentistry and oral and orthopedic surgery is provided in the present invention. Cables and cords are not required; The laser is a microchip whose output wavelength is matched to the peak absorption wavelength of the material to be radiated, and whose output power is adjusted to the specific requirements of the target material. The peak output power of the microchip laser beam is at least 20 mWatts. Energy is not wasted in the lasing materials or by irradiating at an inefficient wavelength, so the efficiency is very high and the power consumption during laser operation is less than 10 Watts. Examples are sterilization lasers and pulsed curing lasers which are ergonomic and lightweight. Other aspects and features of the invention will be more fully apparent from the following disclosure and appended claims.

BRIEF DESCRIPTION OF THE DRAWINGS

FIG. 1A is an enlarged view of section L shown in FIG. 1 showing a microchip laser of the first embodiment.

FIG. 1B is an enlarged view of section L shown in FIG. 1 showing a multiple microchip laser of the second embodiment.

FIG. 1C is an enlarged view of section L shown in FIG. 1 showing a pulsed, passively Q-switched microchip laser of the third embodiment.

DESCRIPTION OF PREFERRED EMBODIMENTS

Figure 1:
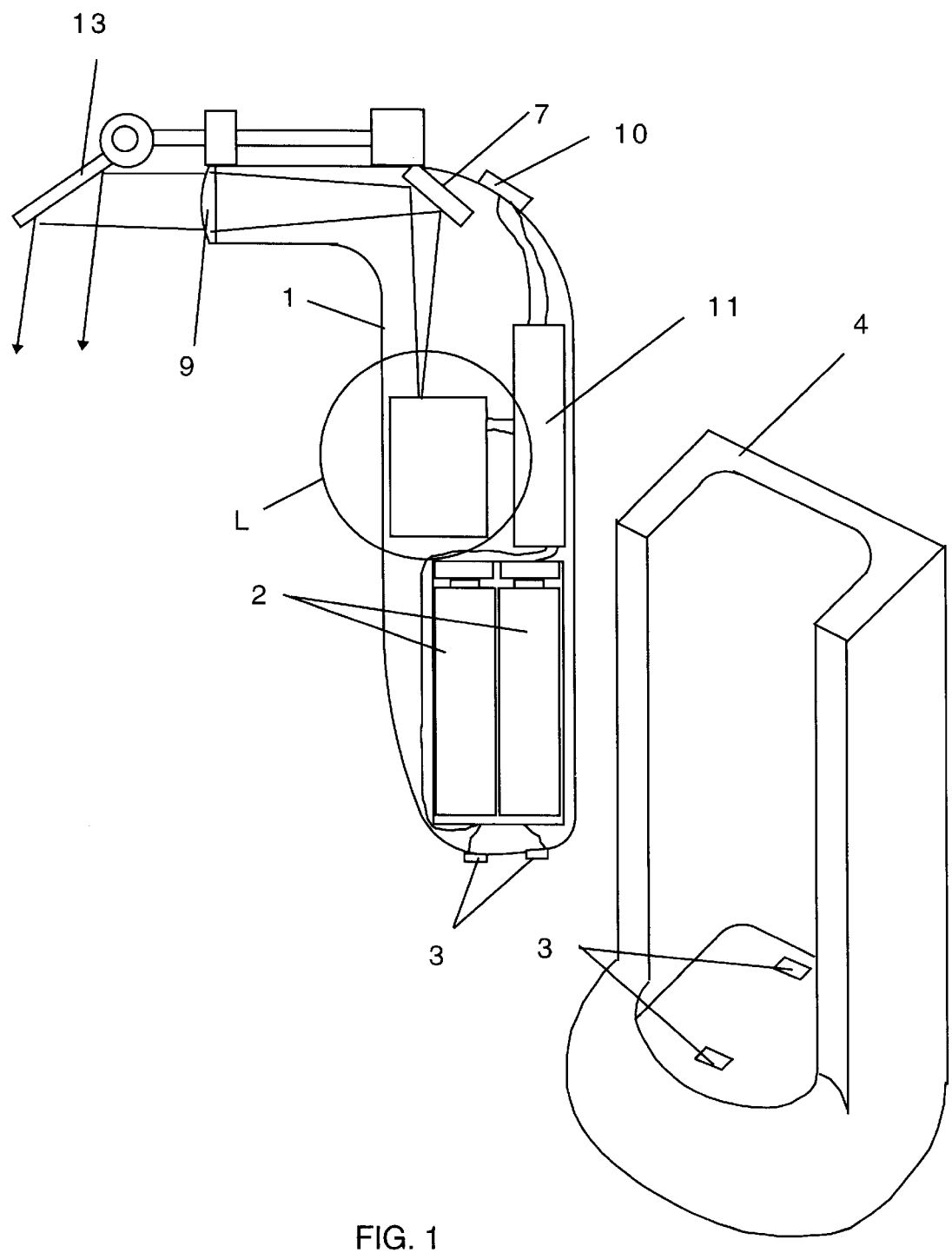
FIG. 1 is a hand-held, self-contained, rechargeable laser dental and surgical instrument.

The present invention is a lightweight, ergonomic, hand-held, cordless, portable, self-contained laser instrument for dentistry, both oral and orthopedic surgery, and medical procedures such as target site sterilization and photo-polymerization curing. The output wavelength from the microchip laser 6 is matched to the peak absorption wavelength of a target material and the output power from the microchip laser 6 is adjusted to the specific requirements of the target material. Examples of medical, surgical, and dental target sites include skin surface, gums, tooth surface, bone surface, bone interior, and the interior tissue of a surgical incision. Another example of a surgical and dental site is material which can be cured by photo-polymerization.

The entire inventive instrument is contained in a single, hand-held, ergonomic housing 1 shown in FIG. 1. It is powered by at least one rechargeable battery 2 which is electrically connected by wires as shown in FIG. 1 to input recharging electrodes 3 sufficient to recharge the unit when it is plugged into a recharger 4. A semiconductor pumping laser 5, electrically connected by wires as shown in FIG. 1 to a variable power diode 11, stimulates laser emission from at least one microchip laser 6 which is in optical contact with the pumping laser 5 as shown in FIGS. 1A, 1B, & 1C. "Optical contact" means oriented in line-of-sight so that laser light from one component shines on and stimulates the next component. Section L in FIG. 1 is shown in detail in FIGS. 1A, 1B, & 1C which are enlarged views of three embodiments of a microchip laser 6 assembly. All of the components shown in FIG. 1 are connected and aligned to each other by being affixed to the inside of the housing 1. There is an internal reflecting means 7 affixed to the inside of the housing 1 in the path of the laser beam for reflecting the laser beam from the microchip laser 6 to deliver it to a target site as shown by the arrows in FIG. 1. The internal reflecting means 7 is one selected from any one of: a mirror; a prism; and an optical fiber. Each microchip laser 6 is constructed of at least two crystals which are joined in an optical contact forming a heterojunction. There is an output filter 8 affixed to the inside of the housing 1 and positioned between the microchip laser 6 and the internal reflecting means 7. There is an output collimating lens 9 affixed at the tip of the housing 1 at an end distal to the internal reflecting means 7. There is a finger tip control button 10 which is control means to turn the laser on and off by switching the electrical current flowing through the wires to the pumping laser 5 on and off as shown in FIG. 1. There is a variable power diode 11 electrically connected by wires to the control button 10, pumping laser 5, and battery 2, which adjusts the output laser power to the specific light absorbing characteristics of a selected target material by varying the electric power flowing from the battery 2. Tunability and temperature control of the microchip laser 6 is provided by a thermo-electric heating and cooling heat exchanger 12 which adjusts the temperature and the index of refraction of the crystals in the microchip laser 6 to tune the output wavelength of the laser beam emitted from the microchip laser 6. There is an external reflecting means 13 which is attached, optionally, to the housing 1, which is capable of being moved into the path of the output laser beam to redirect it toward difficult to reach target sites in the patient. The external reflecting means 13 is selected from any one of: a mirror; a prism; and an optic fiber. The battery 2 is selected such that the power consumption during operation of the laser is at most 10 Watts yielding a capacity of output laser power of at least 20 mWatts. All of the above features are features of each of the following three embodiments of a microchip laser 6 assembly.

The first embodiment of the microchip laser 6 is shown in FIG. 1A and has a single microchip laser 6 constructed, preferably, of the heterojunction crystal, Nd:YAG/KNbO$_3$. This laser emits a wavelength, preferably, of at least 472 nm and at most 474 nm which is useful for curing dental and surgical materials capable of being cured by photopolymerization. In another example of this embodiment the microchip laser 6 is constructed, preferably, of the heterojunction crystal, Nd:YAG/KNbO$_3$/LBO, which emits, preferably, 354 nm to 356 nm wavelength which is useful for sterilization of surgical and dental target sites. Since microbes are far more sensitive to UV light than to visible light, the output power of the inventive sterilization laser can be substantially lower than that of visible light sterilization. In another example of this embodiment active Q-switch electrodes 14 are attached to the KNbO$_3$ of the preferred microchip lasers 6 and to the control button 10 to provide active Q-switching.

In the second embodiment, shown in FIG. 1B, there are two different microchip lasers 6 in optical contact with the pumping laser 5 within the same housing 1 shown in FIG. 1. The microchip lasers 6 are, preferably, Nd:YAG/KNbO$_3$ for curing with 472 nm to 474 nm wavelength laser output, and Nd:YAG/KNbO$_3$/LBO for sterilization with 354 nm to 356 nm wavelength laser output. In another example of this embodiment active Q-switch electrodes 14 are attached to the KNbO$_3$ of the microchip lasers 6 and to the control button. 10 as shown in FIGS. 1 and 1B to provide active Q-switching. There is a switch integrated into the control button 10 for switching between UV and blue laser beam output, so that the same instrument is used for sterilization and for curing by photo-polymerization.

In a third embodiment, shown in FIG. 1C, a saturable absorbing crystal 15, preferably Cr:YAG, is placed in the laser cavity of the at least one of the microchip lasers 6 which allows the laser output to be passively Q-switched. This yields a pulsed laser beam output with high peak power and high efficiency. The advantage is more thorough penetration and curing with better heat dissipation and better control of thermal effects. In one example of this embodiment at least one of the preferred microchip lasers 6 is Nd:YAG/Cr:YAG/KNbO$_3$ which emits an output laser beam wavelength of at least 472 nm and at most 474 nm. In another example of this embodiment at least one of the preferred microchip lasers 6 is Nd:YAG/Cr:YAG/KNbO$_3$/LBO which emits an output laser wavelength of at least 354 nm and at most 356 nm UV light for efficiently sterilizing dental and surgical target sites. In another example more than one pulsed microchip laser 6 is contained in the same housing 1 and there is a switch integrated into the control button 10 for switching amoung the different lasers. Thus, no time is wasted between sterilization and curing steps in a medical procedure.

Accordingly for all these reasons set forth, it is seen that the laser instrument of the present invention represents a significant advancement in the art of microchip, compact, self-contained, hand-held laser instruments for medical surgery, dentistry, and dental surgery, and has substantial commercial merit.

While there is shown and described herein certain specific structures embodying the invention, it will be manifest to those skilled in this art that modifications may be made without departing from the spirit and scope of the underlying inventive concept. The present invention shall not be limited to the particular forms herein shown and described except by the scope of the appended claims.

What is claimed is:

1. A compact, rechargeable, hand-held, laser instrument for use in surgical and dental procedures comprising: a single hand-held housing containing a semiconductor pumping laser, a microchip laser in optical contact with and being pumped by said pumping laser, an internal reflecting means affixed to and within said housing for delivering a laser beam from said microchip laser to a target, an output collimating lens affixed to an end of said housing distal to said internal reflecting means to adjust an output laser beam, at least one rechargeable battery to serve as a sole power supply being electrically connected to input charging electrodes, control means responsive to finger tip pressure affixed to said housing and being electrically connected to said battery and to said pumping laser, and input recharging electrodes sufficient to allow recharging of said battery when said housing is plugged into a recharger, said battery and said pumping laser being selected such that power consumption of said laser instrument during laser operation is at most 10 Watts and such that output power of said output laser beam is at least 20 mWatts, said output power being adjustable to a light absorbing characteristic of said target.

2. The laser instrument of claim 1 wherein said microchip laser generates an output wavelength of at least 472 nm and at most 474 nm, said wavelength is matched to a peak absorption wavelength of said target for photopolymerization of said target, said microchip laser is constructed of Nd:YAG/KNbO$_3$, and said output collimating lens is a planoconvex lens.

3. The laser instrument of claim 1 wherein said microchip laser generates an output wavelength of at least 354 nm and at most 356 nm, said microchip laser is constructed of Nd:YAG/KNbO$_3$/LBO which generates UV light for the purpose of sterilization, and said output collimating lens is a planoconvex lens.

4. The laser instrument of claim 1 wherein there is an output filter affixed to said housing between said microchip laser and said internal reflecting means, and there is an external reflecting means attached to said housing such that said external reflecting means is capable of being moved into a path of said output laser beam to redirect said output laser beam toward difficult to reach target sites.

5. The laser instrument of claim 4 wherein there is a thermo-electric heat exchanger in thermal contact with said microchip laser such that said heat exchanger is capable of controlling the temperature of said microchip laser to tune an output wavelength of said output laser beam generated by said microchip laser, and said housing contains a variable power diode affixed to said housing and electrically connected to said battery and to said control means and to said pumping laser to increase and decrease the output power of the output laser beam to adjust said output power to said light absorbing characteristic of said target.

6. The laser instrument of claim 1 wherein two electrodes are in electrical contact with opposite sides of said microchip laser and with said control means, said electrodes provide active switching modulation of an output wavelength of said microchip laser.

7. A compact, rechargeable, hand-held, multiple microchip laser instrument for surgical and dental procedures comprising: a single hand-held housing containing at least one semiconductor pumping laser in optical contact with at least two microchip lasers, a switching means electrically connected to said lasers for switching from one microchip to another, at least one rechargeable battery being connected electrically to said switching means and to said lasers to serve as a sole power supply during laser operation, input recharging electrodes being connected electrically to said battery and being sufficient to allow recharging of said battery when said housing is plugged into a recharger, at least one internal reflecting means being affixed inside said housing for delivering a laser beam from said microchip lasers to a target, said battery being selected such that a power consumption of said instrument during laser operation is at most 10 Watts and such that output power of an output laser beam is at least 20 mWatts, said output power being adjustable to a light absorbing characteristic of said target.

8. The multiple microchip laser instrument of claim 7 wherein one of said at least two microchip lasers is a UV laser constructed of Nd:YAG/KNbO$_3$/LBO which is useful for sterilization, and another of said at least two microchip lasers is a blue laser constructed of Nd:YAG/KNbO$_3$ which is useful for curing selected materials that are capable of being cured by photo-polymerization, said UV laser emits a wavelength of at least 354 nm and at most 356 nm, and said blue laser emits a wavelength of at least 472 nm and at most 474 nm, said housing contains one output beam filter being affixed inside said housing between said microchip lasers and said internal reflecting means for each of said microchip lasers, said housing contains an output collimating lens affixed to an end of said housing distal to said reflecting means, an external reflecting means is attached to said housing, said external reflecting means is capable of being moved into a path of said output laser beam to redirect said output laser beam toward difficult to reach target sites.

9. The multiple microchip laser instrument of claim 7 wherein at least one of said at least two microchip lasers is in thermal contact with a thermo-electric heat exchanger to provide continuous tunability of an output laser wavelength, said housing contains a variable power diode affixed to inside surface of said housing and electrically connected to said battery and to said switching means and to said pumping laser to control an output power of the output laser beam.

10. The multiple microchip laser instrument of claim 7 wherein two electrodes are in electrical contact with said at least two microchip lasers, said electrodes provide active Q-switched modulation of said output laser wavelength of said microchip lasers.

11. A compact, rechargeable, hand-held, passively Q-switched pulsed laser instrument for surgical and dental procedures comprising: a compact hand-held housing containing at least one microchip laser, a saturable absorbing crystal being disposed in a laser cavity of at least one of said at least one microchip laser to allow an output laser beam to be passively Q-switched, a semiconductor pumping laser in optical contact with said microchip laser, one of said at least one microchip laser being a blue laser having an output beam wavelength matched to a peak absorption wavelength of a selected target material which is capable of being cured by photopolymerization, at least one rechargeable battery being electrically connected to a control means and to said pumping laser to serve as a sole power supply during laser operation, input recharging electrodes being electrically connected to said battery and being sufficient to allow recharging of said battery when said housing is plugged into a recharger, at least one internal reflecting means being affixed inside said housing for delivering a laser beam from said microchip laser to a target, said battery being selected such that a power consumption of said instrument during laser operation is at most 10 Watts and such that an output power of said blue laser is at least 20 mWatts which allows said instrument to be self-contained and hand-held, said output power being adjustable to a light absorption characteristic of said selected target material.

12. The pulsed laser instrument of claim 11 wherein said blue laser is constructed of a microchip of Nd:YAG/Cr:YAG/KNbO$_3$, said blue laser emits a wavelength of at least 472 nm and at most 474 nm, said housing contains at least one output beam filter affixed to an inside surface of said housing and being in optical contact with said microchip laser, one collimating lens affixed to an end of said housing distal to said internal reflecting means, said filter is disposed between said at least one microchip laser and said output collimating lens.

13. The pulsed laser instrument of claim 11 wherein at least one of said microchip laser is a UV laser, said UV laser is constructed of a microchip of Nd:YAG/Cr:YAG/KNbO$_3$/LBO, said UV laser emits a wavelength of at least 354 nm and at most 356 nm which is useful for sterilization.

14. The pulsed laser of claim 11 wherein there is an external reflecting means attached to an exterior surface of said housing being capable of being moved into a path of said output laser beam to redirect said output laser beam toward difficult to reach target sites, said at least one microchip laser is in thermal contact with a thermo-electric heat exchanger which controls both temperature and index of refraction of said microchip laser to provide continuous tunability of the output beam wavelength of said microchip laser, said housing contains a variable power diode affixed to an inside surface of said housing and electrically connected to said battery and to said control means and to said pumping laser to control an output power of said output laser beam, said output power is adjusted to a light absorption characteristic of said selected target material, said control means includes an integrated control means connected electrically to said pumping laser and responsive to finger tip pressure for firing said at least one microchip laser in a pulse form.

* * * * *